United States Patent [19]
Lundbäck

[11] Patent Number: 5,842,985
[45] Date of Patent: Dec. 1, 1998

[54] DEVICE FOR SECURING AN OBJECT TO A SURFACE BY VACUUM

[75] Inventor: Stig Lundbäck, Vaxholm, Sweden

[73] Assignee: Humanteknik AB, Stockholm, Sweden

[21] Appl. No.: 669,971

[22] Filed: Jun. 25, 1996

Related U.S. Application Data

[62] Division of Ser. No. 290,911, Aug. 22, 1994, Pat. No. 5,553,612.

[30] Foreign Application Priority Data

| Feb. 20, 1992 | [SE] | Sweden | 9200516-4 |
| Apr. 28, 1992 | [SE] | Sweden | 9201336-6 |
| Feb. 19, 1993 | [SE] | Sweden | 9203045-1 |

[51] Int. Cl.$^6$ ............................................. A61B 5/0416
[52] U.S. Cl. .............................................. 600/387; 439/41
[58] Field of Search ............................ 128/643, 635–641; 607/149; 439/41, 42; 600/387

[56] References Cited

U.S. PATENT DOCUMENTS

| 3,640,270 | 2/1972 | Hoffmann . |
| 4,369,793 | 1/1983 | Staver et al. . |
| 4,556,065 | 12/1985 | Hoffmann . |
| 4,646,747 | 3/1987 | Lundback . |
| 4,708,381 | 11/1987 | Lundback . |
| 4,736,749 | 4/1988 | Lundback . |
| 4,938,218 | 7/1990 | Goodman et al. . |
| 5,345,935 | 9/1994 | Hirsch et al. . |

FOREIGN PATENT DOCUMENTS

| 0 289 905 | 11/1988 | European Pat. Off. . |
| 0 352 596 | 1/1990 | European Pat. Off. . |
| 0 442 803 | 8/1991 | European Pat. Off. . |
| 39 20 755 | 5/1990 | Germany . |
| 639524 | 12/1978 | U.S.S.R. . |

*Primary Examiner*—Lee Cohen
*Attorney, Agent, or Firm*—Hill & Simpson

[57] ABSTRACT

A reusable electrode holder and associated disposable electrode unit are provided. The holder retains the electrode therein and is connectable to a vacuum source for holding the electrode against a patient's skin with vacuum suction. The holder is also connectable to an electrical lead for connection to the electrode unit. The holder has a resilient cap which is moveable to actuate a valve to open communication through the holder from the vacuum source to a chamber adjacent the skin. To prevent the transfer of contaminants from the skin to reusable parts of the holder, a first contaminant absorber is provided within a housing of the holder and a second contaminant absorber is provided as part of the electrode unit. A second valve can be provided which is actuatable to close vacuum communication when second absorber expands to a threshold contamination condition.

9 Claims, 4 Drawing Sheets

5,842,985

DEVICE FOR SECURING AN OBJECT TO A SURFACE BY VACUUM

CROSS REFERENCE TO RELATED APPLICATION

This application is a division of U.S. patent application Ser. No. 08/290,911, filed Aug. 22, 1994, now U.S. Pat. No. 5,553,612.

BACKGROUND OF THE INVENTION

1. Field of the Invention

This invention relates to a device for vacuum attachment of an object to a surface, such a skin area, especially a device in the form of a suction electrode assembly. More particularly, to present invention relates to a suction electrode assembly for use in taking electro-cardiograms and in carrying out other biophysical examinations and treatments.

A vacuum attachment device of the kind contemplated here is a device which is adapted to be held to a surface under the action of a negative pressure in a vacuum chamber or vacuum cup which is partly delimited by the surface. More particularly, the negative pressure is applied to the vacuum chamber by a vacuum source, such as a suction pump, which is connected to the device.

2. Description of the Related Art

Devices of this kind are embodied in, for example, suction electrode assemblies for use in electrocardiographic and other biophysical examinations in which the surface to which the suction electrode assembly is held is an area of the skin of a patient or other individual. A requirement then to be met is that an electrode which forms part of the electrode assembly is held in good electrical contact with the surface.

Many different embodiments of suction electrode assemblies are known. Examples of embodiments are disclosed in EP-B-0143761, U.S. Pat. No. 4,248,243, DE-A-2548805, AT-C-248608, CH-A-301242.

It is desirable for hygienic and other reasons that it is easy to replace those parts of the electrode assembly which in use of the assembly contact the skin. Such parts can become contaminated by sweat and other skin secretions or by the medium (electrolytic gel) which is used to improve the electrical contact between the electrode and the skin.

Because of the negative pressure and capillary forces, there is a strong tendency for the contaminants to undesirably penetrate into certain regions of the electrode assembly. These regions include where the assembly is connected with the vacuum source and with the electrical lead connecting the electrode with the electrical measuring equipment. The contaminants also promote the growth of microorganisms.

In practice, a replacement of the entire electrode device after each examination is not practical, because an electrode device which is adapted to be attached by vacuum is rather expensive. This is true especially when the electrode device includes a valve between the vacuum port and the vacuum chamber. This valve serves to disconnect the vacuum chamber from the vacuum port when the electrode device is not applied to the skin.

In practice, therefore, the replacement in the first instance must be limited to components which can be supplied at a sufficiently low cost and are most likely to become contaminated. That is, replaced parts preferably include at least those components which are in direct contact with the skin and are therefore unavoidably contaminated in use. Naturally, these components include the electrode and the sealing skirt or the like which delimits the area of the skin subjected to the negative pressure.

For that reason, the electrode device has to be constructed such that there is little likelihood of contaminants reaching those parts of the electrode device which are not replaced after each use, so that the electrode device can be used many times before it is necessary to replace or clean those parts which are not replaced after each use.

SUMMARY OF THE INVENTION

An object of the invention is to provide a device, especially a vacuum electrode device, which meets these requirements and is also uncomplicated and user friendly.

These and other requirements are met by a device made in accordance with the present invention.

The invention also relates to an electrode unit for use as a disposable component in a vacuum electrode device, particularly a vacuum electrode device.

To these ends, the present invention provides a device including an object holder and an associated object held therein. The object holder is configured to retain the object against a surface by vacuum pressure. The object holder includes a vacuum port.

The object holder also includes a sealing member which is engageable with the surface to define a vacuum chamber. A vacuum passage extends between the vacuum chamber and the vacuum port. A first contaminant absorber is disposed in the vacuum chamber.

In an embodiment, the absorber is disposed in the vacuum chamber at a junction between the vacuum chamber and the vacuum passage.

In an embodiment, the holder further includes a socket. A connector member is configured to be received in the socket. The absorber, the object, and the connector member form a unit which is releasably connectable with the socket.

In an embodiment, the absorber is disk-shaped.

In an embodiment, the connector member extends through the absorber and includes a free end portion which protrudes from one side of the absorber.

In an embodiment, the unit includes a layer which engages the sealing member. The layer extends over one side of the absorber and is provided with one or more air flow-through openings.

In an embodiment, the layer is positioned at the side of the absorber from which the free end portion of the connector member protrudes.

In an embodiment, the sealing member includes an annular sealing skirt which extends about the vacuum chamber. The sealing member also has an outer sealing rim for cooperation with the surface and an inner sealing rim which is directed toward the object holder. The inner sealing rim is sealingly engageable with a coacting sealing surface on the object holder by a force directed towards the object holder and acting on the outer sealing rim.

In an embodiment, a second contaminant absorber is disposed in the vacuum passage.

In an embodiment, the device further includes a valve disposed in the vacuum passage and biased towards a closed position.

In an embodiment, the valve has a valve seat and a valve member which coacts with the valve seat. The valve member is movable relative to the valve seat between a closed position and an open position. An actuating member is connected with the valve member and forms a movable wall of an air chamber that communicates with the vacuum passage between the valve seat and the vacuum chamber.

For a more detailed explanation of the invention, reference is made to the following description of an embodiment, more particularly a vacuum electrode device, which is shown by way of example in the drawings.

DETAILED DESCRIPTION OF THE PRESENTLY PREFERRED EMBODIMENT

Figure 1:
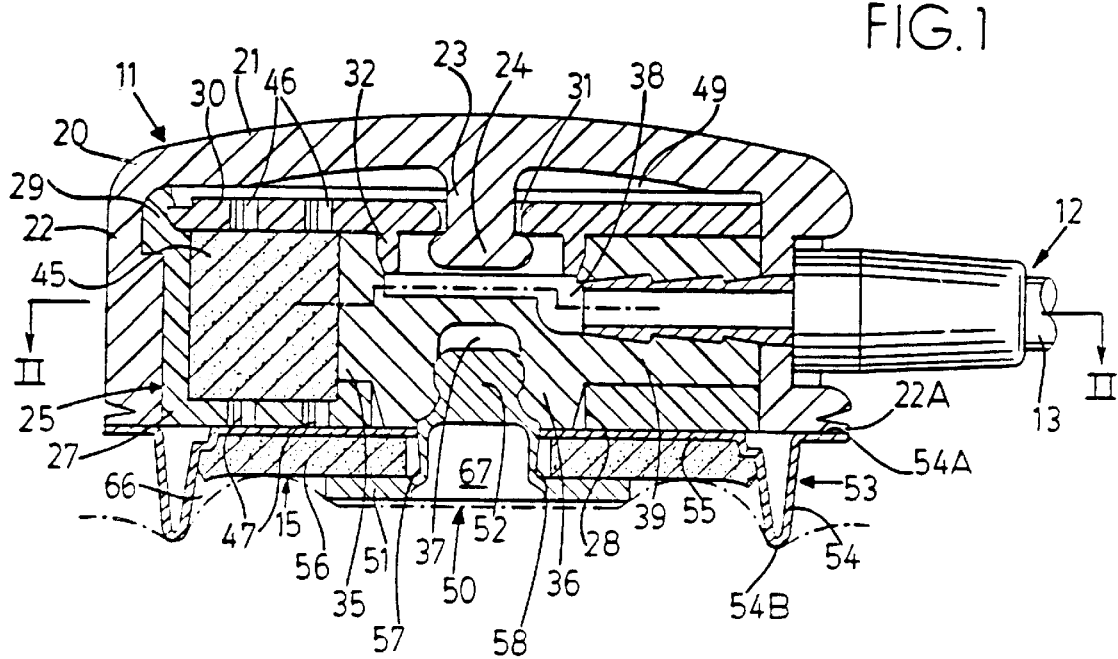
FIG. 1 is a vertical sectional view of a first embodiment of the electrode device with a vacuum conduit and a signal lead connected to it.

As shown in the drawings, the vacuum electrode device includes an object holder, generally designated by 11 and constituting an electrode holder which is intended to be used several times. The holder 11 is adapted for connection to an assembly 12 including a vacuum conduit 13 and an electrical signal lead 14. The vacuum electrode device also includes an electrode unit 15 which is intended to be used as a disposable component and adapted to be secured within the electrode holder as a held object.

The electrode holder 11 comprises an enclosure which is made of a resilient material, preferably a silicon polymer material, and is in the shape of a casing or cap 20 which is open at the bottom and has a slightly domed top wall 21. In a generally circular cylindrical side wall 22 of the cap, an inlet for the connection of the conduit and lead assembly 12 is provided.

An underside of the top wall 21 of the cap is provided with a centrally positioned, downwardly directed short stem portion 23 with a head 24 at its free end.

Moreover the electrode holder 11 includes a housing 25 which is received in the cap 20. The housing 25 includes a side wall 26 and a bottom wall 27. The housing 25 is open at the upper side and provided with a central opening 28 in the bottom wall 27. The side wall 26 of the housing is generally circular and cylindrical but does not extend all the way round, so that there is a gap at the inlet for the connection of the conduit and lead assembly 12.

Adjacent an upper edge of the side wall 26 of the housing 25 there is shoulder for a cover plate 30 with which the open upper side of the housing can be closed. The cover plate 30 has a central aperture 31 forming a valve seat in which the stem portion 23 of the cap 20 can be inserted. The underside of the cover plate 30 is provided with a downwardly projecting annular neck or stub tube 32 encircling the central aperture 31.

The electrode holder 11 also includes a connector block 35 which is inserted in the housing 25 and made of an electrically conducting resilient material, e.g. a silicon polymer material. The connector block 35 is fitted between the bottom wall 27 of the housing and the cover plate 30.

An electrode contact portion 36 on the connector block 35 projects downwardly through the central opening 28 of the bottom wall 27 of the housing and is provided with an electrode socket 37 in the shape of a downwardly open blind hole.

On the upper side of the connector block 35, opposite the electrode socket 37, there is a cavity into which the annular neck 32 of the cover plate 30 projects downwardly to define together with the connector block a vacuum chamber 38. The annular neck 32 seals against the wall of the vacuum chamber.

A shank 39 extends laterally from the portion of the connector block 35 which is provided with the electrode socket 37 and the vacuum chamber 38. This shank 39 is provided with a passage 40 which extends to the vacuum chamber 38 and receives a male vacuum connector 41 of a connector assembly 42 which forms part of the conduit and lead assembly 12.

By way of the male vacuum connector 41 inserted into the shank passage 40 through the inlet in the side wall 26 of the cap, and the vacuum conduit 13 attached to the male vacuum connector, the vacuum chamber 38 can be connected with a suction pump or other vacuum source (not shown).

The connector assembly 42, in which the male vacuum connector 41 is inserted and to which the vacuum conduit 13 is secured, is also provided with a contact pin 43, which is electrically connected with the electrical signal lead 14. The latter is secured to the connector assembly 42 and physically joined with the vacuum conduit 13. At the end thereof remote from the connector assembly 42, the signal lead 14 is provided with means for connecting the signal lead to measuring equipment, such as an electrocardiograph (not shown).

When the male vacuum connector 41 protruding from the connector assembly 42 is plugged into the shank passage 40 of the connector block 35, the contact pin 43 is simultaneously inserted in the shank 39 by the side of the shank passage so that an electrical contact is established between the connector block 35 and the signal lead 14.

Moreover, the electrode holder 11 comprises an absorber body 45 which is inserted in the housing 25 and preferably is permeable to air and forms a filter. The absorber body 45 fills the cavity, generally horseshoe-shaped in plan view, which is defined by the side wall 26 and bottom wall 27 of the housing, the cover plate 30 and the connector block 35.

Figure 3:
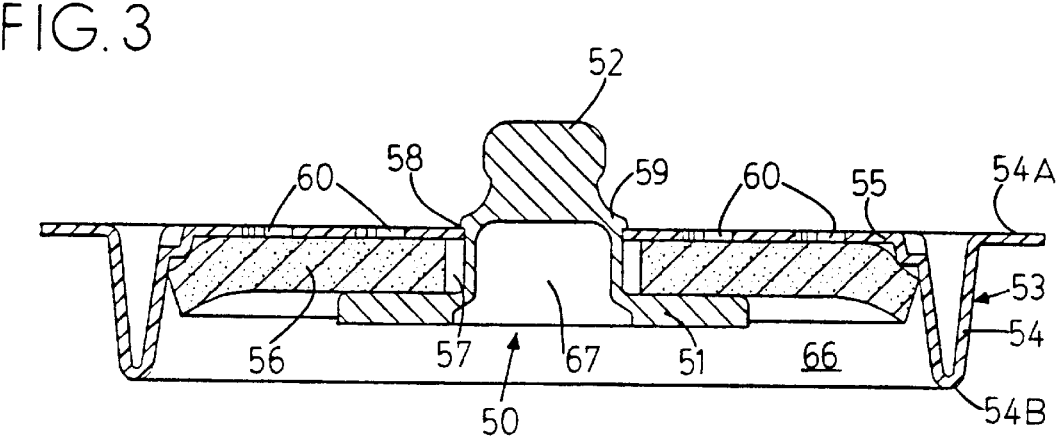
FIG. 3 is a sectional view of an electrode unit according to the invention which is intended for use as a disposable component in a vacuum electrode device.

The electrode unit 15, which is shown detached from the electrode holder 11 in FIG. 3, comprises three separably interconnected parts, namely (i) an electrode member (silver-silver chloride electrode) 50 with an electrode plate 51 and a contact knob 52 projecting from the electrode plate 51, (ii) a sealing member 53 having an annular sealing skirt 54 and a perforated end wall 55, and (iii) an outer absorber body 56 which is disposed inwardly of the sealing skirt 54 between the end wall 55 of the sealing member and the electrode plate 51 of the electrode member 50.

The contact knob 52 of the electrode member extends through central apertures 57 and 58 in respectively the absorber body 56 and the end wall 55 of the sealing member and fits snugly in the central aperture of the end wall so that the three parts do not easily detach from each other by themselves. The holding together of the three parts is strengthened by an annular protrusion 59 on the contact knob 52.

A number of openings 60 in the form of holes or slits are provided in the end wall 55 of the sealing member 53 so that air can flow from the space 66 circumscribed by the sealing skirt 54 beneath the outer absorber body 56 and the electrode member 50 to the space 49 formed in the electrode holder 11 between the cover plate 30 and the top wall 21 of the cap 20.

The assembled electrode unit 15 is connected with the electrode holder 11 by pressing the contact knob 52 of the electrode member 50 into the socket 37 formed in the resilient connector block 35. An interlocking interconnection is then established because the socket 37 has an internal restriction and the contact knob 52 is provided with a corresponding waist. When the contact knob 52 is inserted, the connector block 35 is slightly expanded at the socket 37, and this ensures a reliable holding of the electrode unit 15 and also a good electrical contact between the electrode member 50 and the connector block 35 and consequently, between the electrode member 50 and the signal lead 14.

When the electrode unit 15 is connected to the electrode holder 11, the free upper end of the sealing skirt 54, which is U- or V-shaped in cross-section, will engage the underside of a sealing lip 22A on the lower edge of the side wall 22 of the cap. This sealing lip and the upper end of the sealing skirt 54, namely an outwardly directed flange 54A on the sealing skirt, then seals off the space circumscribed by the sealing skirt.

To carry out a measurement using the electrode device after the electrode unit 15 has been attached to the electrode holder 11 as described and, if necessary, a layer of electrolytic gel or the like has been applied to the underside of the electrode plate 51, the electrode device is positioned on the proper area of the skin of the patient or person being examined so that the free lower end 54B of the sealing skirt 54 engages the skin.

By a slight pressure against the top wall 21 of the cap 20, the sealing skirt 54 is pressed against the skin so that its lower end 54B seals off the air space 66 circumscribed by the sealing skirt 54 and so that the underside of the electrode plate 51 contacts the skin.

At the same time, the flexible top wall 21 of the cap 20 is displaced downwardly, so that the headed stem portion 23 on the top wall 21 is displaced downwardly within the central aperture 31 in the cover plate 30. This opens a free air passage between the vacuum chamber 38 in the connector block 35 and the space 49 between the cover plate 30 and the top wall 21 of the cap. The negative pressure in the vacuum chamber 38 will then act throughout the underside of the top wall 21 of the cap so that the top wall remains displaced downwardly and the air passage defined between the vacuum chamber 38 and the space 49 above the cover plate 30 by the central aperture 31 of the cover plate remains open. The underside of the head 24 of the stem portion 23 engages the bottom wall of the vacuum chamber 38 so that the negative pressure can always act throughout the underside of the top wall 21 of the cap 20.

Opening of the air passage also results in sucking away air from the space circumscribed by the sealing skirt 54, that is, the vacuum chamber 66, between the skin of the person being examined and the outer absorber body 56 and the electrode plate 51, and this space consequently is placed under a negative pressure. The electrode device is therefore held to the skin by the atmospheric pressure acting on the upper side of the top wall 21 of the cap with the electrode plate 51 engaging the skin as is indicated by a dash-dot line in FIG. 1.

While the electrode device is held to the skin, the negative pressure in the vacuum chamber 66 is maintained even if ambient air should leak into the vacuum chamber past the sealing skirt 54. Sweat, electrolytic gel and other contaminants on the skin are captured by the absorber body 56.

On completion of the measurement the electrode device is detached from the skin by equalizing the pressure in the space 49 beneath the top wall 21 with the pressure of the ambient air; this can be done e.g. by tilting the electrode holder 11 so that a greater amount of ambient air is permitted to enter beneath or above the sealing skirt 54 to remove or substantially reduce the negative pressure in the vacuum chamber 66.

As a result of the equalization of the pressure, the top wall 21 of the cap is moved upwardly to its original position under the action of its inherent resiliency so that the head 24 of the stem portion 23 engages the circumferential edge of the aperture 31, which edge forms a valve seat. The head 24, acting as a valve member, closes the air passage between the vacuum chamber 38 and the space 49 between the cover plate 30 and the top wall 21 of the cap. The negative pressure still acts on the stem portion 23 but the surface area on which the negative pressure acts is so small that the upward force developed by the top wall prevails.

After the electrode device has been detached, the electrode unit 15 is removed by hand and a new electrode unit is inserted.

The valve device which is formed by the cap 20 and the cover plate 30 can of course be used independently, that is, in vacuum electrode devices or vacuum attachment devices other than those shown and described here.

Contaminants appearing at the location where the electrode device is attached to the skin—such contaminants mostly are in the form of sweat exuded on the skin and electrolytic gel spreading beside the electrode plate 51—are captured completely or at least to the greater part by the outer or primary absorber body 56 in the electrode unit 15 which is intended to be used only once or at most a few times.

If moisture and other contaminants should migrate past the electrode unit 15, these contaminants will be captured by the inner or secondary absorber body 45 inside the electrode holder 11. This absorber body may serve as a bacterial or viral filter and may contain an indicator which signals when it is time to replace the entire object holder 11.

There is therefore very little danger that contaminants from the skin of the person being examined will reach the cover plate 30 and be transported still farther, up to the vacuum chamber 38 and the male vacuum connector 41. Both the vacuum conduit 13 and the electrical junction of the signal lead 14 with the connector assembly 42 are therefore very well protected against contamination.

The electrical contact site between the contact knob 52 of the electrode element 50 and the electrode socket 37 of the connector block 35 is well protected, because this contact site is remote from the area where air and existing contaminants are transported.

Figure 4:
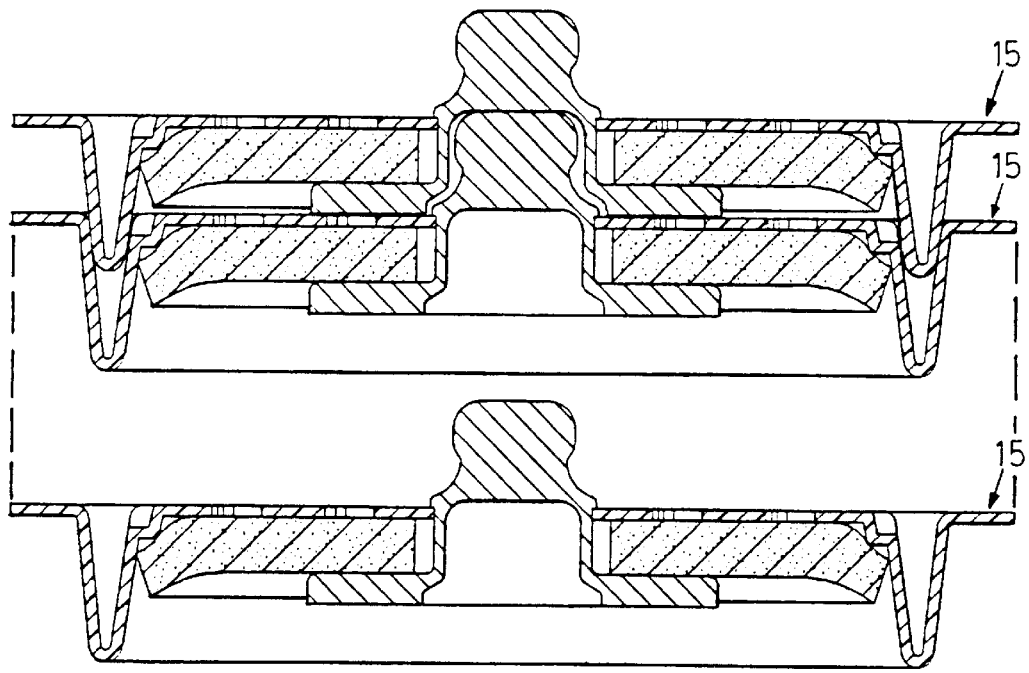
FIG. 4 is a sectional view of a stack of electrode units of the design shown in FIG. 3.

As is apparent from FIGS. 3 and 4, the electrode unit 15 is constructed such that it can be stacked with other, similar electrode units in a space-saving manner. The stackability is achieved firstly because the electrode member 50 is provided with a cavity 67 which opens into the underside of the electrode plate 51 and which extends into the contact knob 52, and secondly because the sealing skirt 54 is in the form of an annular fold which is open at its upper end. Thereby the contact knob on the electrode member 50 of an underlying electrode unit 15 can extend into the electrode member of an overlying electrode unit, and the sealing skirt 54 of the underlying electrode unit can receive the lower portion of the sealing skirt of the overlying electrode unit.

Preferably, the outer or primary absorber body 56 is permeable to air so that it can act as a filter. It is not necessary, however, that it is permeable to air; what is essential is only that it is capable of capturing and retaining those contaminants which should be prevented, as far as possible, from migrating past the electrode unit.

If the absorber body 56 is not permeable to air, the arrangement must allow any air leaking inwardly beneath the sealing skirt 54 to flow past the absorber body. This requirement can be met in a simple manner e.g. by providing the sealing skirt 54 and/or the end wall 55 with lugs, grooves, ribs or other formations which permit air to bypass the absorber body. It may be suitable to provide such formations even if the absorber body is permeable to air. Air may then pass even if the absorber body should be more or less clogged, e.g. by fluid which it has absorbed, electrolytic gel, etc.

It is within the scope of the invention to integrally combine in a disposable electrode unit an absorber. The function of such an embodiment is that which has been described in respect of the absorber body 56 in the described exemplary embodiments. Particularly, the function is to keep contaminants of one kind or other away from the part which is intended to be used repeatedly, that is, the electrode holder 11 in the exemplary embodiment, with an electrode element which functionally corresponds to the electrode element 50 in the exemplary embodiment. The electrode element need not necessarily initially have the electrical property required for the electrode function. For example, it may be constructed or arranged such that the conductivity required for the electrode function is brought about by preparation of the integrated absorber-electrode member directly prior to use thereof, such as by soaking it with an electrolytic gel.

It has been found that under certain conditions in use of an electrode unit of the construction shown in FIG. 1, an undesirable effect appears, where that the absorber body too efficiently carries away moisture also from the skin area contacted by the electrode. This results in a transition resistance between the electrode and the skin which is larger or which varies in an undesirable manner.

This problem may arise particularly when a measurement is carried out without an electrolytic gel or other creamy or viscous substance having good electrical conductivity being applied to the electrode or the skin. In such cases it is important that the skin beneath the electrode is not too dry, that is, that the moisture which is present or is exuded under the electrode is not carried away.

In the embodiment of the electrode unit shown in FIG. 3 it may happen that the absorber body also removes too much moisture from the skin area beneath the electrode, although the absorber body does not directly engage this skin area, but only the skin area beside the electrode.

In accordance with the present invention this problem is solved by spacing or isolating the absorber body from the electrode contact surface by means of a non-absorbing member. This means that the absorber body is essentially prevented from having an absorbing effect on the skin area adjacent the skin area which is contacted by the electrode, so that it absorbs moisture only at a certain distance outwardly from the contact surface, or when the moisture leaves the surface of the skin.

This impeding effect can be brought about in different ways, such as by providing a substantially moisture-tight layer which covers an area around the electrode contact surface so that the absorbing material of the absorber body will not directly engage the skin in that area.

The layer may be a separate piece of a film which is positioned e.g. between, on the one hand, the electrode part forming the electrode contact surface, on the side of that part which is directed away from the contact surface, and, on the other hand, a portion of the absorber body which overlaps that electrode part, the layer extending sufficiently far beyond the electrode part to cover a sufficiently large area of the skin. Naturally, it is also possible to apply such a separate layer in other ways.

Moreover, the layer may be integrally combined with the absorber body, which in such case comprises an impermeable layer at that area and on that side which in use engages the skin area immediately outwardly of the electrode contact surface. This impermeable layer may be produced by surface coating or other treatment of the absorber such that the layer is substantially impermeable to moisture.

The absorbing effect of the absorber body naturally has to be spaced from the electrode contact surface by a sufficient distance, or separated from the skin surface such that the capillarity is interrupted, to ensure that moisture is not transported to any substantial extent along the skin surface from the electrode contact surface and over the separating distance. In practice, it may be suitable for the entire or almost the entire surface, i.e the underside, of the absorber body positioned adjacent the skin surface to have a separate impermeable layer, or an impermeable layer integrated in the absorber body, such that only the portion of the absorber body located farthest from the electrode absorbs moisture from the skin. It has been found that this is quite sufficient for an efficient carrying-away of sweat and other contaminants to take place.

Figure 2:
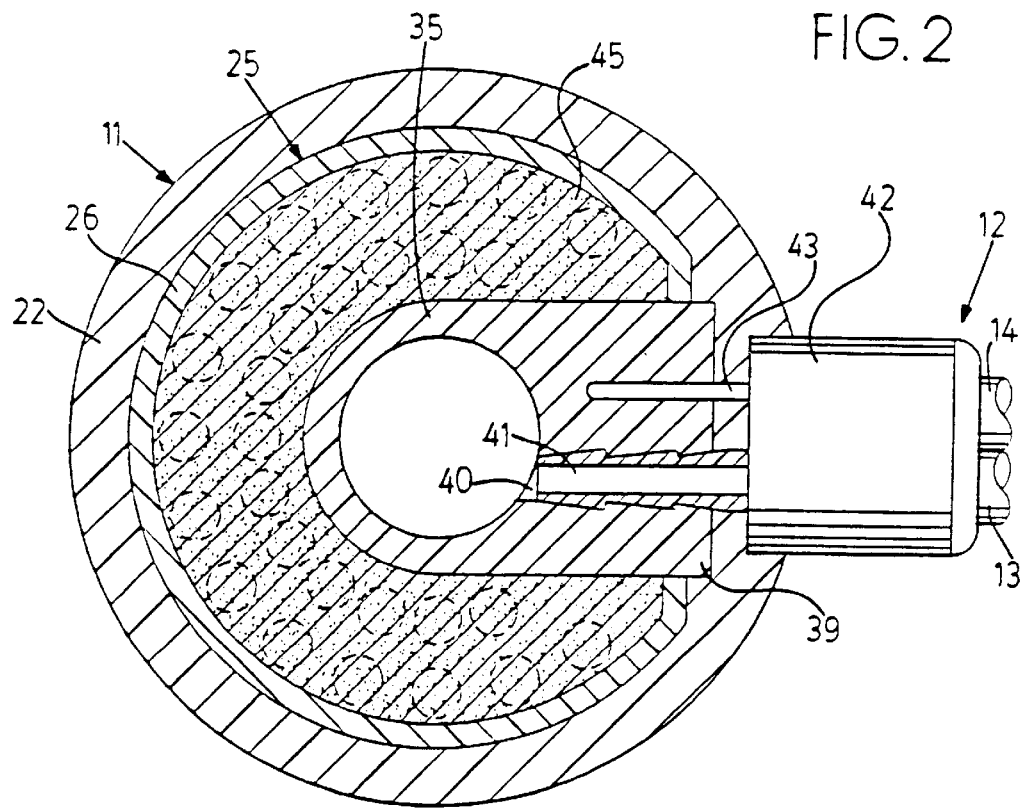
FIG. 2 is a sectional view taken generally along line II—II in FIG. 1.
Figure 5:
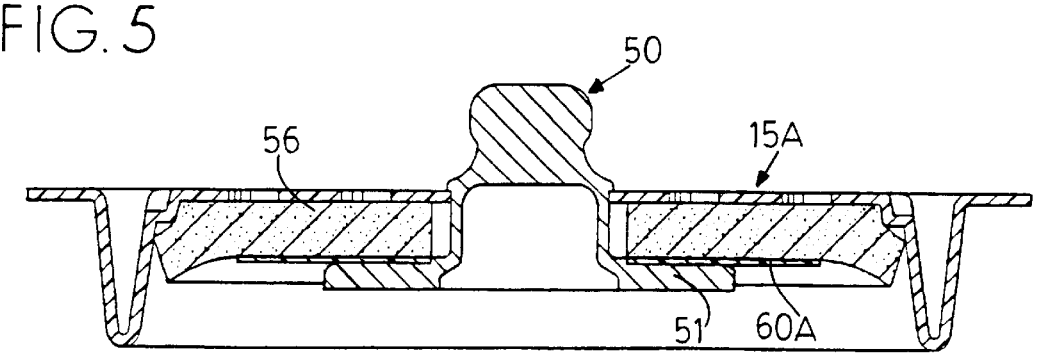
FIG. 5 and FIG. 6 show modified embodiments of the electrode unit in FIG. 3.
Figure 6:
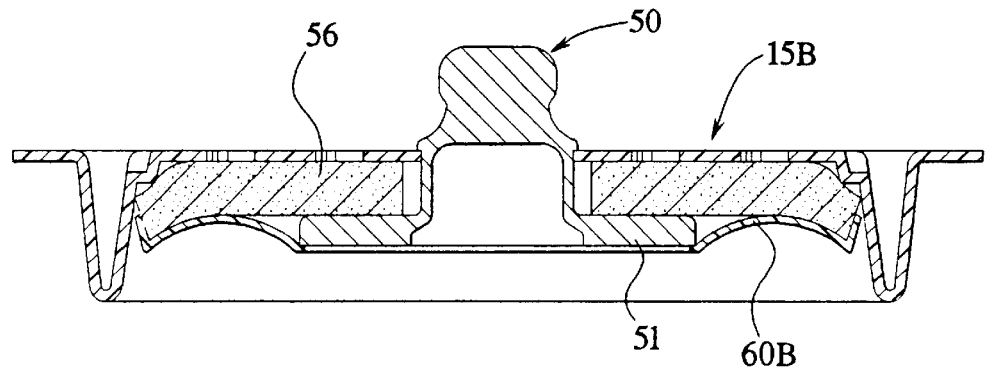

FIGS. 5 and 6 show two modified embodiments of the electrode unit of FIG. 3 which are useful in the vacuum electrode device of FIG. 1 and 2 in cases where it is important to avoid the absorber body carrying away moisture from the skin area contacted by the electrode.

In the electrode unit 15A shown in FIG. 5 a non-absorbing (capillarity-interrupting) member designated by 60A is applied to the underside of the absorber body 56 to prevent the absorber body from applying its absorbing effect direct to the skin within a circular area the periphery of which is spaced from the electrode plate of the electrode 50.

The spacing may vary but should be sufficient to ensure that the absorber body 56 does not cause any substantial carrying-away of moisture from the contact surface between the electrode plate 52 and the skin. It has been found in practice that it is suitable to arrange for the non-absorbing member to extend up to or almost up to the periphery of the absorber body 56 so that the absorber body does not directly engage the skin except adjacent the periphery. The ability of the absorber body to transport moisture horizontally inwardly above the non-absorbing member ensures that the carrying away of contaminants from the skin is still sufficiently efficient.

The non-absorbing member 60A may be a separate member, such as an annular piece of plastic film, which is loosely inserted between the electrode plate 52 and the overlying portion of the absorber body 56. However, it may also be an integral part of the absorbing body proper. In such case it may be produced by coating or otherwise preparing the absorber body over a smaller or larger portion of the surface thereof with a suitable material which seals the pores at the underside. It would also be possible to bring about the desired lack of absorbing ability by heat treatment of the absorber body.

In the electrode unit 15B shown in FIG. 6 the non-absorbing member 60B is a layer, such as a plastic film, which is secured to the electrode plate 51 along its periphery and extends outwardly from the periphery and along the underside of the absorber body 56 at least far enough to prevent carrying-away of moisture from the contact surface between the electrode plate and the skin.

Figure 7:
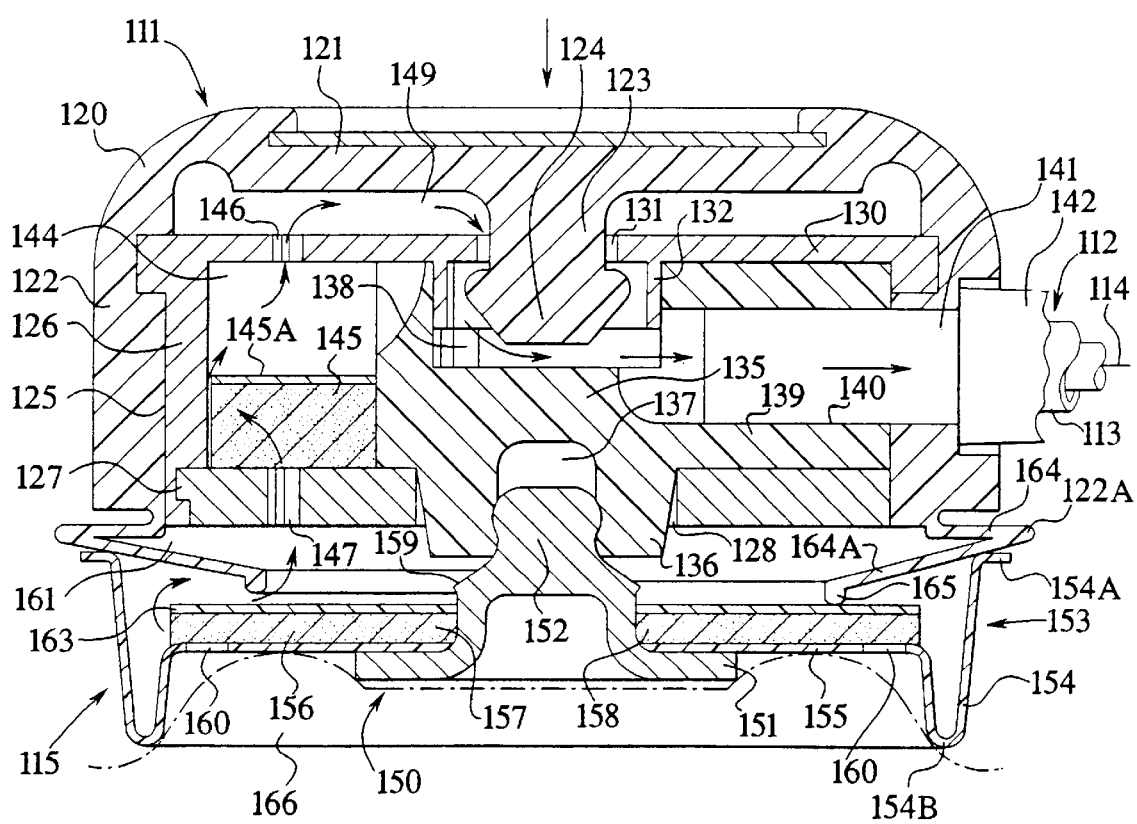
FIG. 7 is a view corresponding to FIG. 1 and shows another embodiment of the electrode device.
Figure 8:
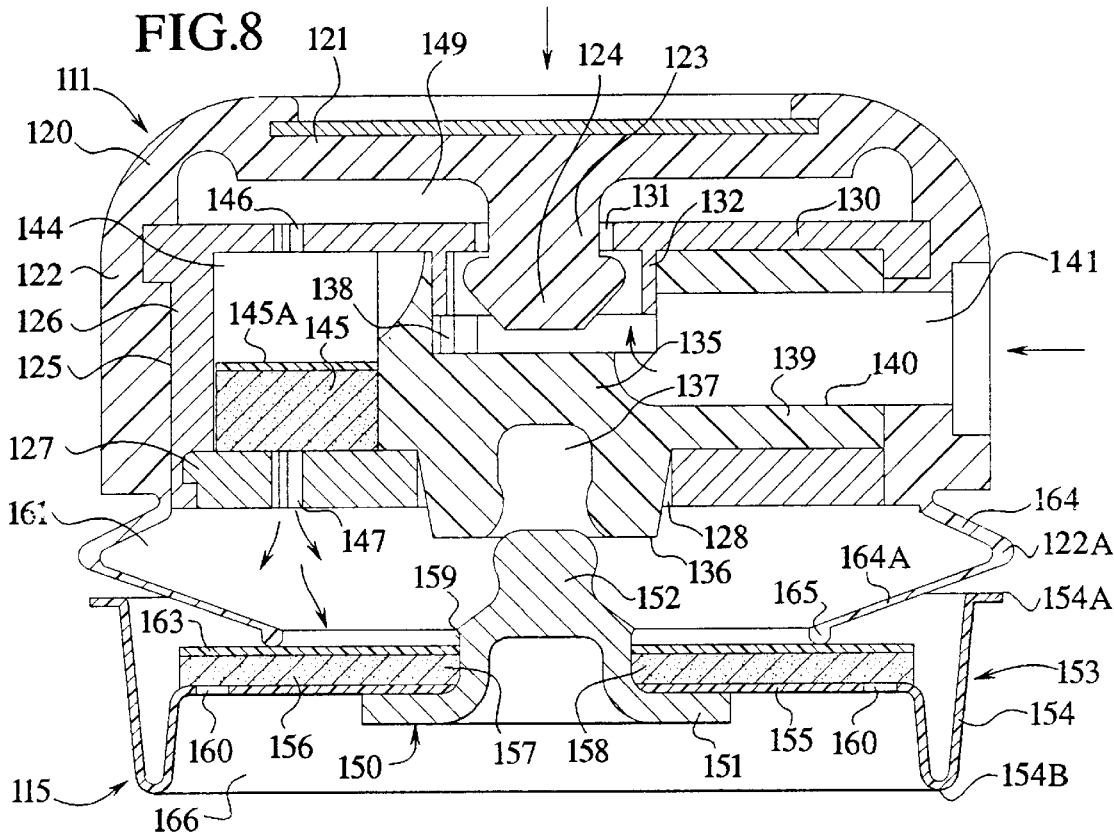
FIG. 8 shows the electrode device of FIG. 7 in a condition in which an electrode device is detached under the action of overatmospheric pressure.
Figure 9:
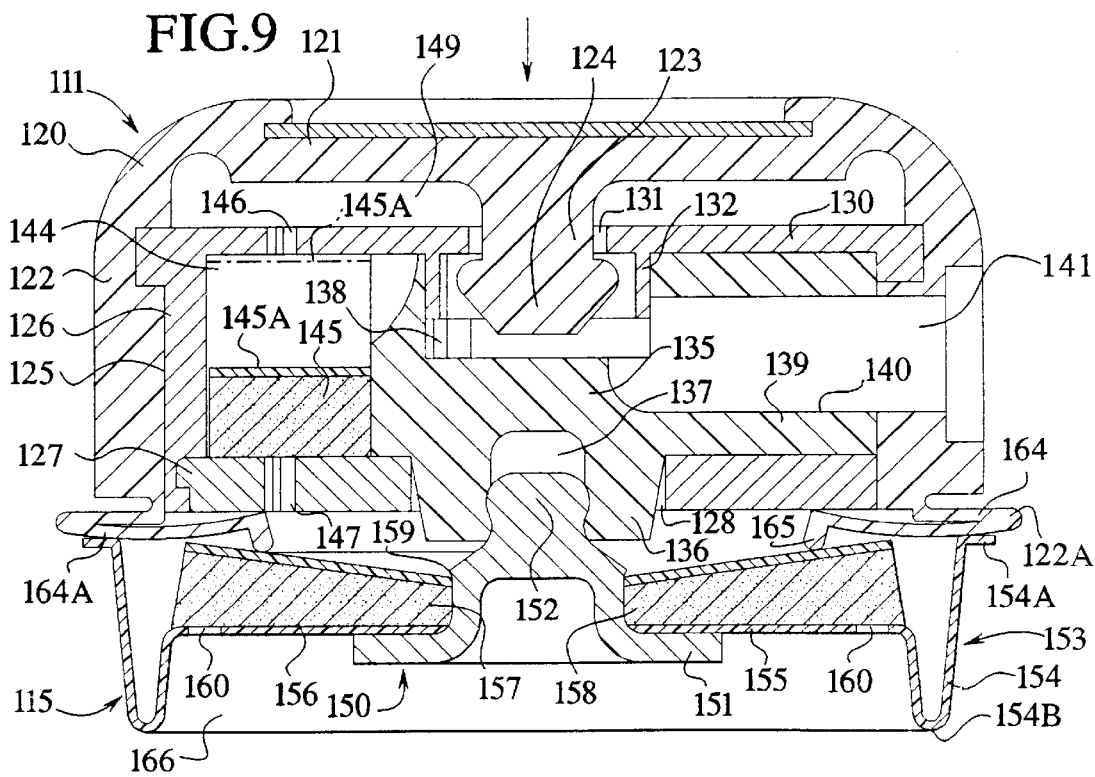
FIG. 9 shows the electrode device of FIG. 7 in an "alarm" condition.

The electrode device shown in FIGS. 7–9 incorporates additional modifications of both the electrode holder and the electrode unit. Those parts shown in FIGS. 7–9 which have equivalents in FIGS. 1–3 are designated by the reference numerals used in FIGS. 1–3 supplemented with the prefix 1.

In the embodiment shown in FIGS. 7–9, the housing 125 is somewhat different from the housing 25 of FIG. 1 in that its top wall 130 is integral with the side wall 126, whereas its bottom wall 127 is a separate plate which is snapped into a recess adjacent the lower edge of the side wall.

As is explained in greater detail below, in certain cases the chamber 138 defined between the central portion of the housing top wall 130 with its depending annular neck 132 and the connector block 135 will be under a negative pressure and in other cases will be under an overatmospheric pressure. The end of the air conduit 113 which is remote from the male connector 141 is therefore adapted to be connected to a suction and pressure pump or other source of negative and positive fluid pressure (not shown).

Apart from that, the differences between the electrode device of FIGS. 7–9 and the electrode device of FIGS. 1–3 primarily relate to the construction and arrangement of the absorber body 145, the sealing lip 122A and the absorber body 156 associated with the electrode unit 115. In this case, the last-mentioned absorber body is positioned on the upper side of the end wall 155 of the sealing member 153.

Initially, the absorber body 145 only fills a portion, namely the lower portion, of the U- or horseshoe-shaped cavity 144 in the housing 125. This absorber body consists of a moisture absorbing material which expands as the absorbed amount of moisture increases. When a certain amount of moisture has been absorbed, the absorber body has expanded sufficiently for its upper side to engage the underside of the housing top wall 130 and thereby block the air flow-through openings 146; an impermeable layer 145A provided on the upper side of the absorber body at least in the area registering with the air flow-through openings contributes to an effective sealing.

When the just-mentioned situation arises and the absorber body 145 thus blocks the openings 146, the negative pressure which normally exists in the chamber 138 and which is communicated to these openings when the passage 131 in the top wall 130 is open, is unable to cause air to flow from the cavity 144 through the openings 146. This condition is utilized in the manner described below to indicate that the absorber body 145 should be replaced.

The absorber body 156 is in the shape of a thin, circular disk, which is loosely positioned on and covers substantially the entire upper side of the end wall 155 of the sealing member 153 and thus also covers the openings 160 in the end wall, which openings are located at the outer portion of the end wall. The upper side of the absorber body 156 is provided with an impermeable cover, preferably in the shape of a thin plastic disk 163, which is engaged with the contact knob 152 of the electrode member 151 in a substantially air-tight manner. The cover is continuous, that is, it has no perforations or openings at least over its central portion, and it may suitably be imperforate over the entire area from the contact knob up to or substantially up to the outer periphery.

The sealing lip 122A is formed of two annular, disk-shaped parts, an outwardly directed upper part 164, the inner periphery of which is joined with the housing side wall 122, and a substantially wider lower part 164A, the outer periphery of which is joined with the outer periphery of the upper part and which when relieved from outer forces extends obliquely downwardly into the air space 161. The lower part ends with an annular bead 165, which is adapted to sealingly engage the upper side of the disk 163. The lower lip part is very flexible, and a small differential pressure across the lip is thus sufficient to move the lip upwardly or downwardly. Because of its large width, the lower lip part may remain in engagement with the disk 163 even when the electrode member is displaced downwardly relative to the holder 111 to be detached therefrom as is described in greater detail below.

When a measurement is to be carried out using the electrode device after the electrode unit 115 has been snapped in position on the electrode holder 111 and, when necessary, a layer of electrolytic gel or the like has been applied to the underside of the electrode plate 151, the electrode device is positioned at the proper place on the skin of the patient or the person being examined, so that the free lower end 154B of the sealing skirt 154 is engaged with the skin.

A slight pressure on the top wall 121 of the cap 120 causes the sealing skirt 154 to be pressed against the skin so that its lower edge 154B seals off the air chamber 166 circumscribed by the sealing skirt 154 and also causes the underside of the electrode plate 151 to engage the skin.

At the same time, the flexible top wall 121 of the cap 120 is displaced downwardly so that the headed stem portion 123 on the top wall 12 is displaced downwardly within the central aperture 131 in the cover plate 130. This will open a free air passage between the chamber 138 in the connector block 135 and the space 149 between the cover plate 130 and the top wall 121 of the cap. The negative pressure existing in the chamber 138 will then act throughout the underside of the top wall 121 of the cap and cause the top wall to remain depressed so that the air passage which is defined by the central aperture 131 of the cover plate and interconnects the vacuum chamber 138 and the space 149 above the cover plate 130 remains open. The underside of the head 124 of the stem portion abuts the bottom wall of the vacuum chamber 138 so that closing of the passage defined by the aperture 131 is avoided and so that it is ensured that the negative pressure can always act throughout the underside of the top wall 121 of the cap 120.

Opening of the air passage also causes air to be sucked away from the space, the air chamber 166, circumscribed by the sealing skirt 154 between, on the one hand, the skin of the person being examined and, on the other hand, the absorber body 156 and the electrode plate 151 so that negative pressure is applied to this chamber, see FIG. 7. Air is sucked out of the air chamber 166 through the openings 160, the passage defined beneath the slightly raised lower lip part 164A, the air space 161, the openings 147 in the lower housing wall 127, the cavity 144 holding the absorber body 145, the openings 146 in the top wall 130 of the housing, the space 149, the aperture 131 in the housing top wall 130, the chamber 138 and the connecting passage 140. The electrode device is thereby held to the skin by the air pressure acting on the upper side of the top wall 121 of the cap, the electrode plate 151 engaging the skin as is indicated by a dash-dot line in FIG. 7.

While the electrode device is applied to the skin, the negative pressure is maintained in the air chamber 166 even if some ambient air should leak into the air chamber past the sealing skirt 154. At least the major portion of sweat, electrolytic gel and other contaminants on the skin are captured by the absorber body 156, since these contaminants pass the outermost portion of the absorber body.

On completion of the measurement, the electrode device is detached from the skin by equalizing the pressure in the space 149 beneath the top wall 121 with the ambient air pressure, e.g. by tilting the electrode holder 111 such that a greater amount of ambient air is permitted to flow beneath or above the sealing skirt 154 to remove or substantially reduce the negative pressure in the air chamber. Naturally, it is also possible to disconnect the vacuum source so that the unavoidable leakage of air causes the electrode device to detach more or less by itself.

The equalization of the pressure causes the top wall 121 of the cap 120 to return upwardly to its original position under the influence of its inherent resiliency so that the head 124 of the stem portion 123 engages the edge around the aperture 131, which forms a valve seat. The head 124, acting as a valve member, closes the air passage between the chamber 138 and the space 149 between the cover plate 130 and the top wall 121 of the cap. The negative pressure still acts on the stem portion 123, but the surface area of the stem portion subjected to the negative pressure is small so that the upward force developed by the top wall prevails.

After the electrode device has been detached, the electrode unit 115 is removed and a new electrode unit is inserted.

FIG. 8 illustrates how the electrode unit can be removed in a very convenient manner without touching it with the fingers by supplying air under a certain overatmospheric pressure to the electrode device through the air conduit 113 and the connecting passage 140. When carrying out ECG measurements, for example, a large number of electrodes are used at the same time, and with the construction according to the invention, all electrode units can be removed simultaneously by a single manipulation, namely by switching the source of air, which is common to all electrode units, from vacuum to overatmospheric pressure. The person operating the equipment can hold the bundle of air conduits with the electrode devices above a waste recipient so that the used electrode units drop into this recipient when they are detached from the electrode holder.

As indicated above, the outer side of the downwardly directed annular neck 132 on the housing top wall 130 sealingly engages the circumferential wall of the air chamber 138. This circumferential wall, which is formed by the upper portion of the resilient connector block 135, is shaped in such a way over at least a portion of its circumference that it yields resiliently under the action of a sufficient overpressure in the air chamber 138 and, acting as a one-way valve, can pass air from the air chamber to the adjacent absorber body cavity 144.

When pressurised air is supplied to the chamber 138 by way of the connector passage 140, the air can therefore flow between the outer side of the annular neck 132 and the air chamber wall and then past the upper edge of the latter, through the cavity 144 accommodating the absorber body 145, and the holes 147 in the housing bottom wall 127 into the air space 161 between the underside of the bottom wall 127 and the upper side of the electrode member 115. The lower sealing lip part 164A, which then acts as a one-way valve, is pressed against the upper side of the disk 163 to prevent air from escaping from the air space 161.

The downward force which the air in the air space 161 applies to this sealing lip part and on the portion of the electrode member 115 located inwardly of the sealing lip part, pushes the electrode member downwardly so that the snap fastener formed by the electrode contact portion 136 and the contact knob 152 on the electrode member is separated. As soon as the electrode contact portion 136 has disengaged the contact knob 152, the electrode member 115 drops, suitably into a waste receptacle.

The relatively large width of the sealing lip part 164A and its flexibility ensure that the annular bead 165 remains in sealing engagement with the electrode member 115 until the latter has been detached, even if it should become somewhat tilted during the downward movement as a result of unsymmetrical loading by the air pressure.

Contaminants at the location where the electrode device is applied to the skin—such contaminants mostly are in the form of sweat exuding from the skin and electrolytic gel spreading outwardly of the electrode plate 151—are captured completely or at least substantially completely by the outer or primary absorber body 156 in the electrode unit 115 which is intended to be used only once or at most a few times.

FIG. 9 illustrates a condition which arises if the absorber body 156 in the electrode unit 115 expands substantially as a consequence of substantial absorption of moisture; this may happen for example if the operator fails to replace the electrode unit as often as intended, that is, normally after a single use. This condition is of a character such that continued use of the electrode device is impossible and thereby indicates that it is necessary to replace the electrode unit.

The absorber body 156 continues to expand with increasing amount of absorbed moisture. It thereby raises the overlying impermeable disk 163 which in turn lifts the lip part 164A. When the disk 163 has been raised sufficiently, the annular bead 165 of the sealing lip 164A will seal both against the underside of the bottom wall 127 and the upper side of the disk 163.

When this happens, the negative pressure cannot be communicated beyond the air space 161. Because of inward leakage of air, the electrode device then can no longer be held to the skin. This will of course immediately be noticed and provides a "alarm" signal to the operator who is thus made aware that the electrode unit has to be replaced with a new one.

The absorber body 156 associated with the electrode unit 115 may thus be regarded as a kind of primary filter, which prevents sweat and other contaminants from migrating past the electrode unit and into the electrode holder 111.

If moist and contaminants should nevertheless be able to pass the electrode unit 115, these contaminants will be captured by the inner or secondary absorber body 145 inside the electrode holder 111. This absorber body may if desired serve as a bacterial or viral filter.

There is consequently very little danger of contaminants from the skin of the person being examined reaching the cover plate 130 and migrating farther, up to the air chamber 138 and the male vacuum connector 141. Both the air conduit 113 and the electrical connection of the signal lead 114 with the connector assembly 142 are therefore well protected against contamination.

As contaminants are captured and retained by the absorber body 145, this body expands so that its upper side and the impermeable layer 145A thereon will finally engage the housing top wall 130 and block the flow-through openings 146 therein. This is indicated by dash-dot lines in FIG. 9. The condition which thereby arises provides an indication that it is time to discard the electrode holder. This condition manifests itself in that the electrode device is impossible to apply in the usual manner on the skin area on which a measurement is to be carried out, because the negative pressure in the air chamber 138 cannot be communicated to the air chamber 166 beneath the electrode member 115. Disassembly of the electrode holder and replacement of the absorbing body 145 is possible but hardly justified.

As in the preceding embodiments both absorber bodies 145 and 156 may incorporate a so-called superabsorbent, which is characterised by a very great ability to quickly absorb large amounts of moisture.

It should be understood that various changes an modifications to the presently preferred embodiments described herein will be apparent to those skilled in the art. Such changes and modifications may be made without departing from the spirit and scope of the present intention and without diminishing its attendant advantages. It is, therefore, intended that such changes and modifications be covered by the appended claims.

I claim:

1. An object holder for vacuum retainment of an object against a skin surface, the object holder comprising:

a socket configured to receive the object;

a vacuum port;

a vacuum passage which extends between the vacuum port and a surface of the object holder adapted to engage an annular sealing member of the object to define therewith a vacuum chamber;

a valve disposed in the vacuum passage and biased toward a closed position; and a support in operational contact with the socket which limits movement of the socket and the object held thereby during vacuum retainment of the object.

2. An object holder according to claim 1, wherein the valve comprises:

a valve seat;

a valve member which coacts with the valve seat and is movable relative to the valve seat between a closed position and an open position; and a movable wall which is connected with the valve member to actuate the valve, the movable wall defining a side of an air chamber that communicates with the vacuum passage between the valve seat and the vacuum chamber.

3. An object holder according to claim 2, further comprising:

a housing defining a rigid wall disposed within the vacuum passage, wherein the support extends from the housing, the valve seat being provided at one side of the housing and the support being provided at another side of the housing.

4. An object holder according to claim 2 wherein a side of the moveable wall directed away from the air chamber is subjected to ambient air pressure external of the object holder.

5. An object holder according to claim 1, wherein the object is either an electrode or a transducer for use in carrying out biophysiological examinations and treatments, and wherein the socket is made of electrically conducting resilient material and includes means for connection to an electrical signal lead.

6. A device having an object holder for vacuum attachment of an object to a surface, the object holder comprising:

a vacuum port;

a vacuum passage in fluid communication between the vacuum port and a surface of the object holder adapted to engage an annular sealing member of the object to define therewith a vacuum chamber;

a valve positionable in a closed position to block the vacuum passage and positionable in an open position to allow a negative pressure into the vacuum passage;

a containment absorber disposed in the vacuum passage;

whereby the containment absorber is expandable by absorption of moisture so that an expansion of the containment absorber closes off the vacuum passage and equalizes the negative pressure which thereafter actuates the valve to the closed position.

7. A device according to claim 6, wherein the absorber is enclosed in the object holder in a cavity defined by a wall having a fluid through-flow opening, the absorber being expandable in said cavity from a first condition in which the absorber is spaced from the wall to a second condition in which the absorber engages the wall to cover the fluid flow-through opening.

8. A device having an object holder for vacuum attachment of an object to a surface, the object holder comprising:

a vacuum port;

a vacuum passage in fluid communication between the vacuum port and a surface of the object holder adapted to engage an annular sealing member of the object to define therewith a vacuum chamber;

a valve positionable in a closed position to block the vacuum passage and positionable in an open position to allow a negative pressure into the vacuum passage;

a containment absorber disposed in the vacuum passage, the containment absorber being expandable by absorption of moisture; and a valve member attached to the valve which is displaceable to a sealing position in response to expansion movement of the absorber wherein the valve is simultaneously moved to the closed position.

9. A device according to claim 8, wherein the valve member is an annular lip, the lip having an outer portion attached to the object holder and an inner portion which is sealingly engageable both with a side of the object holder directed towards the object and with a fluid-impermeable wall member on the side of the absorber directed towards the object holder.

* * * * *